US00PP16464P3

(12) United States Plant Patent
Moore

(10) Patent No.: US PP16,464 P3
(45) Date of Patent: Apr. 18, 2006

(54) *FORSYTHIA* PLANT NAMED 'MCKCITRINE'

(50) Latin Name: *Forsythia viridissima*
Varietal Denomination: McKCitrine

(75) Inventor: Daniel Moore, Waterloo, WI (US)

(73) Assignee: McKay Nursery Co., Inc., Waterloo, WI (US)

( * ) Notice: Subject to any disclaimer, the term of this patent is extended or adjusted under 35 U.S.C. 154(b) by 115 days.

(21) Appl. No.: 10/918,932

(22) Filed: Aug. 16, 2004

(65) Prior Publication Data

US 2006/0037119 P1 Feb. 16, 2006

(51) Int. Cl.
*A01H 5/00* (2006.01)

(52) U.S. Cl. ..... Plt./230

(58) Field of Classification Search ..... Plt./230
See application file for complete search history.

*Primary Examiner*—Anne Marie Grunberg
(74) *Attorney, Agent, or Firm*—Penny J. Aguirre

(57) ABSTRACT

A new cultivar of *Forsythia viridissima* 'McKCitrine' characterized by its unique foliage that is variegated with lime green centers and chartreuse margins.

2 Drawing Sheets

Genus/species: *Forsythia viridissima.*
Varietal denomination: 'McKCitrine'.

BACKGROUND OF THE INVENTION

The present invention relates to a new and distinct cultivar of *Forsythis viridissima* and will be referred to hereafter by its cultivar name, 'McKCitrine'. 'McKCitrine' represents a new cultivar of *Forsythia*, a deciduous shrub grown for landscape use.

The inventor discovered the new cultivar, 'McKCitrine', in a nursery in Waterloo, Wis. in July of 2000. 'McKCitrine' arose as a naturally occurring branch sport on a plant of *Forsythia viridissima* 'Bronxensis' (not patented). 'McKCitrine' was selected for its unique foliage that is characterized by variegated leaves with lime green centers and chartreuse margins. The parent plant, 'Bronxensis' has foliage that is darker green in color and non-variegated. 'McKCitrine' is further characterized by its compact growth habit, a characteristic derived from 'Bronxensis'. The only other *Forsythia viridissima* cultivar with variegated foliage known to the inventor is the cultivar 'Variegata' (not patented) with foliage that is green with white mottling. There are a few cultivars of *Forsythia×intermedia* cultivars that have variegated foliage, however they exhibit plant habits that are not as compact as 'McKCitrine'.

Asexual reproduction of the new cultivar was first accomplished by softwood cuttings in Waterloo, Wis. in July of 2000 by the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'McKCitrine' from other varieties of *Forsythia* known to the inventor.

1. The foliage of 'McKCitrine' has leaves that emerge mainly chartreuse in color and mature to a variegated pattern of lime green centers with chartreuse margins. The chartreuse margins may change to creamy white as the leaves age when grown in full sun.
2. The plant habit of 'McKCitrine' is compact, with short internodes, and a mounded habit.
3. 'McKCitrine' is small in stature, reaching a mature height of about 61 cm (2 ft) and a spread of about 76 cm (2.5 ft).
4. Flowering has not been observed under the conditions tested.

BRIEF DESCRIPTION OF THE DRAWING

The accompanying photographs were taken of a two year old plants of 'McKCitrine' as grown outdoors under full sun in Waterloo, Wis. and are representative of the of the new cultivar 'McKCitrine'.

The photograph on the first sheet was taken in May as grown in a two-gallon container while the photograph on the second sheet was taken in mid summer.

The colors in the photograph are as close as possible with conventional photography and the color readings given in the botanical description most closely describe the new cultivar.

BOTANICAL DESCRIPTION OF THE PLANT

The following is a detailed description of a two year-old plant of the new cultivar as grown in a two-gallon container under natural light (full sun), outdoors in Waterloo, Wis. Phenotypic differences may be observed with variations in environmental, climatic, and cultural conditions. The color determination is in accordance with the 2001 R.H.S. Colour Chart of The Royal Horticultural Society, London, England, except where general color terms of ordinary dictionary significance are used.

Botanical classification: 'McKCitrine' is a cultivar of *Forsythia viridissima.*

Parentage: Naturally occurring branch sport of *Forsythia viridissima* 'Bronxensis'.

General description:

*Plant habit.*—Compact, mounded, deciduous shrub.

*Height and spread.*—61 cm in height and 76 cm in spread.

*Hardiness.*—USDA Zone 4.

*Culture.*—Tolerant to most soils in full sun to part shade. Full sun is required for best foliage color.

*Diseases and pests.*—No susceptibility or resistance to other diseases or pests known to effect *Forsythia viridissima* has been observed.

*Root description.*—Fibrous.

Growth and propagation:

*Propagation.*—Softwood stem cuttings.

*Root initiation.*—7 to 14 days when grown at 20 to 25° C. in a greenhouse without supplemental lighting under mist or high humidity. 1200 PPM IBA applied to base of cuttings enhances rooting.

*Time required for root development.*—4 to 6 weeks of root development is required before shifting into a 2 gallon container. A 2-gallon container is marketable in 2 years.

Stem description:

*Shape shape.*—Round, solid.

*Stem color.*—New wood; 144A turning to an intermediate color between 144A and 146B then 146A. Old wood; 146A with an overlay of 148D as the stem becomes woody.

*Stem diameter.*—Typically about 1.5 to 2 mm in new growth, up to 7 mm in diameter at base.

*Stem surface.*—Glabrous on younger stems, becomes glaucous in appearance with small nodules on woody stems.

*Internode length.*—Typically 1.5 to 2 cm (0.5 to 2 cm between leaves).

*Branching.*—About 7 to 9 basal branches on 2 year old plants, typically 7 to 10 secondary branches (often in opposite pairs) on a 30 cm branch without pinching. Suckers from the crown grow upright and should be headed back. Pinching increases branching and reduces internode lengths. Branches typically range 10 to 22 cm in length.

Foliage description:

*Leaf shape.*—Oblanceolate.

*Leaf division.*—Simple.

*Leaf base.*—Attenuates to petiole.

*Leaf apex.*—Acute.

*Leaf venation.*—Upper surface; conspicuous, typically 3 to 4 pairs of lateral veins from midrib, color consistent with margin color. Lower surface; Not conspicuous, vein color consistent with color of leaf centers.

*Leaf margins.*—Serrated, average of 8 serrations per side on a leaf 5 cm in length.

*Leaf attachment.*—Petiolate.

*Leaf arrangement.*—Opposite.

*Leaf surface.*—Glabrous on upper and lower surfaces.

*Leaf length.*—4 to 5 cm (mature leaves, not including petiole).

*Leaf width.*—1 to 1.5 cm (mature leaves).

*Leaf emergence.*—Leaf out is typically observed about the first week in May in Wisconsin.

*Leaf color.*—Immature: New leaves in spring often emerge solid 2C (yellow) and develop into margins and centers as they mature. After margins develop (about a week) and newly emerged leaves in mid summer have the following color pattern. Upper; margins are N144A to N144B (yellow-green) with centers 144A (darker yellow-green), Lower; margins N144A with centers N144A, margins are not as conspicuous. Mature: Upper; margins range from 145A to 144A to 144B to 155B with centers ranging from 137B to 138B. Lower; margins range from 147B to 147C with centers 147B, margins are not as conspicuous as upper surface. Margins on mature leaves are typically 2 to 5 mm in width.

*Petiole size.*—1 to 1.5 cm in length, about 1 mm in width.

*Petiole shape.*—Sulcate.

*Petiole color.*—144A.

*Stipules.*—Very small, at base of petioles, remains as buds (not leafy).

Flower and seed production: Flowering has not been observed under the conditions tested.

It is claimed:

1. A new and distinct cultivar of *Forsythia* plant named 'McKCitrine' substantially as herein illustrated and described.

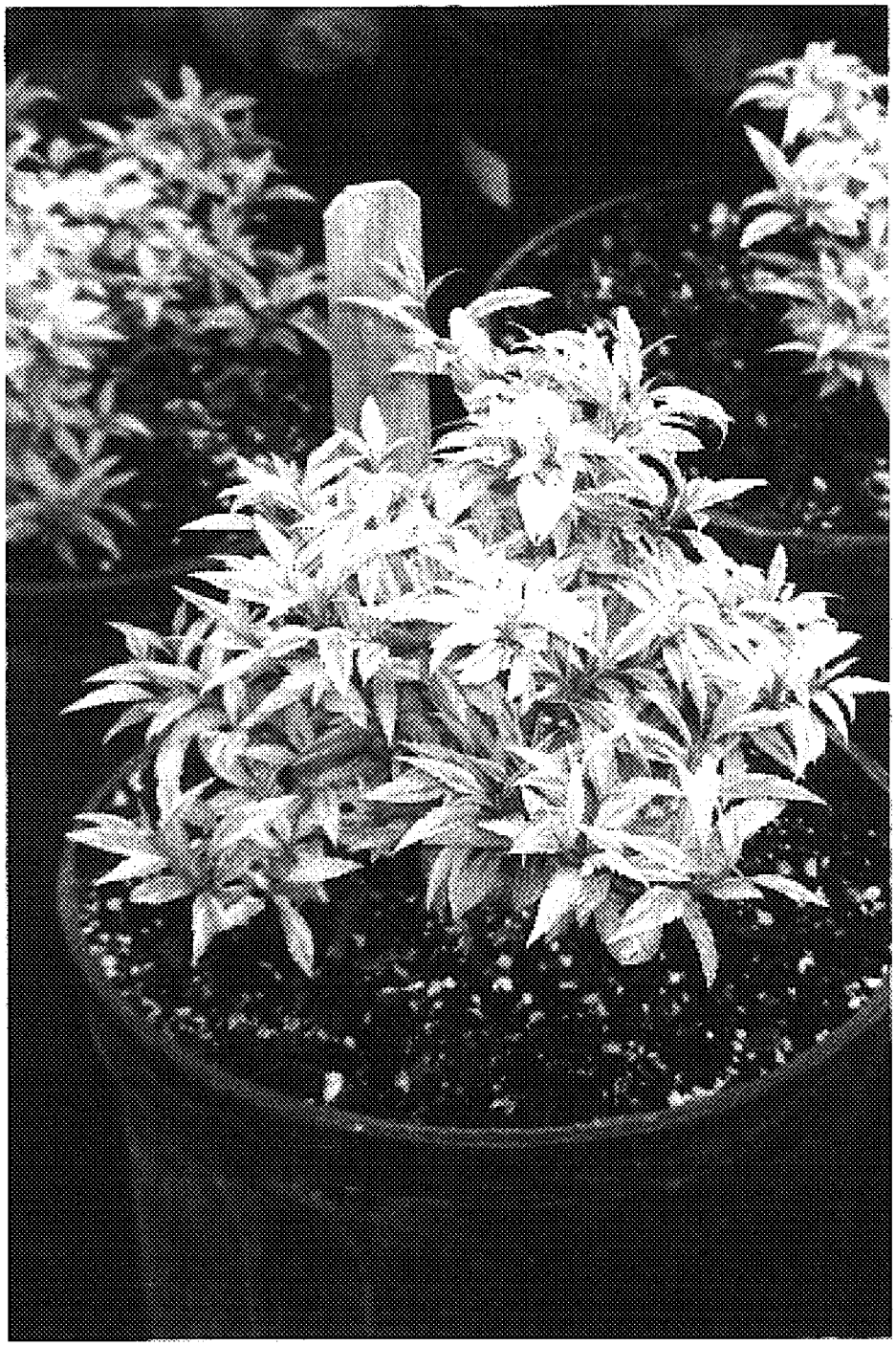

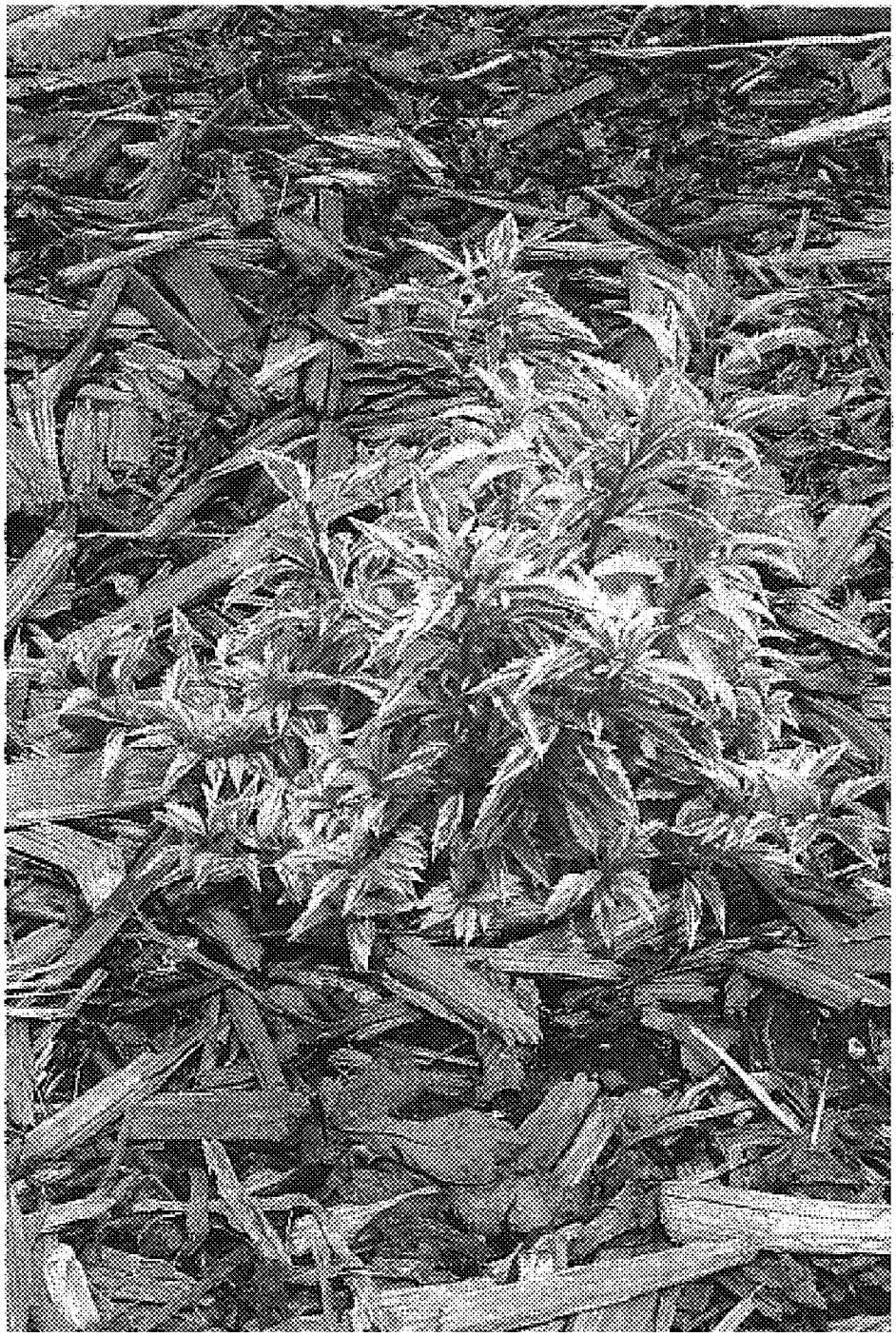

* * * * *